(12) United States Patent
Deconinck et al.

(10) Patent No.: US 7,931,697 B2
(45) Date of Patent: Apr. 26, 2011

(54) COMPOSITION COMPRISING 2,3-DIAMINO-6,7-DIHYDRO-1H,5H-PYRAZOLO[1,2-A]PYRAZOL-1-ONE AND 4,5-DIAMINO-1-(β-HYDROXYETHYL)PYRAZOLE, KITS CONTAINING SAID COMPOSITION, AND PROCESS FOR DYEING THEREWITH

(75) Inventors: Gautier Deconinck, Saint Gratien (FR); Jean-Baptiste Saunier, Paris (FR); Patricia Desenne, Bois Colombes (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/613,890

(22) Filed: Nov. 6, 2009

(65) Prior Publication Data
US 2010/0251489 A1    Oct. 7, 2010

Related U.S. Application Data

(60) Provisional application No. 61/115,640, filed on Nov. 18, 2008.

(30) Foreign Application Priority Data

Nov. 6, 2008    (FR) ..................................... 08 57541

(51) Int. Cl.
*A61Q 5/10* (2006.01)
(52) U.S. Cl. ............. 8/405; 8/406; 8/410; 8/421; 8/435; 8/570; 8/573
(58) Field of Classification Search ............... 8/405, 406, 8/410, 421, 435, 570, 573
See application file for complete search history.

(56) References Cited

U.S. PATENT DOCUMENTS

| | | |
|---|---|---|
| 2005/0028302 A1 | 2/2005 | Audousset et al. |
| 2006/0003028 A1 | 1/2006 | Myers et al. |
| 2008/0005853 A1 | 1/2008 | Cottard et al. |
| 2008/0163883 A1 | 7/2008 | Cottard et al. |
| 2009/0007347 A1* | 1/2009 | Cottard et al. ................ 8/409 |
| 2009/0151090 A1 | 6/2009 | Audousset |

FOREIGN PATENT DOCUMENTS

| | | |
|---|---|---|
| EP | 1 764 082 A2 | 3/2007 |
| EP | 1 870 083 A2 | 12/2007 |
| EP | 1 927 376 A1 | 6/2008 |
| EP | 1 927 377 A1 | 6/2008 |
| EP | 2 060 301 A2 | 5/2009 |
| FR | 2 886 141 A1 | 12/2006 |

OTHER PUBLICATIONS

Co-pending Application filed Nov. 6, 2009.
French Search Report for FR 0857541, dated Aug. 28, 2009.
French Search Report for FR 0857539, dated Aug. 27, 2009.
English language abstract of FR2 886 141 A1, Dec. 1, 2006.
Office Action mailed Jul. 20, 2010, in co-pending U.S. Appl. No. 12/613,911.

* cited by examiner

*Primary Examiner* — Eisa B Elhilo
(74) *Attorney, Agent, or Firm* — Finnegan, Henderson, Farabow, Garrett & Dunner, LLP

(57) ABSTRACT

The present disclosure relates to a composition for dyeing keratin fibers, comprising, in a suitable medium, at least one first oxidation base chosen from 2,3-diamino-6,7-dihydro-1H,5H-pyrazolo[1,2-a]pyrazol-1-one and the addition salts thereof; and at least one second oxidation base chosen from 4,5-diamino-1-(β-hydroxyethyl)pyrazole and the addition salts thereof. The present disclosure also relates to a process for dyeing keratin fibers using the composition of the present disclosure, the use of this composition for dyeing keratin fibers, and also a method for making the composition of the present disclosure.

14 Claims, No Drawings

COMPOSITION COMPRISING 2,3-DIAMINO-6,7-DIHYDRO-1H,5H-PYRAZOLO[1,2-A]PYRAZOL-1-ONE AND 4,5-DIAMINO-1-(β-HYDROXYETHYL)PYRAZOLE, KITS CONTAINING SAID COMPOSITION, AND PROCESS FOR DYEING THEREWITH

This application claims benefit of U.S. Provisional Application No. 61/115,640, filed Nov. 18, 2008, the contents of which are incorporated herein by reference. This application also claims benefit of priority under 35 U.S.C. §119 to French Patent Application No. FR 0857541, filed Nov. 6, 2008, the contents of which are also incorporated herein by reference.

The present disclosure relates to a composition for dyeing keratin fibers, for example human keratin fibers such as the hair, comprising 2,3-diamino-6,7-dihydro-1H,5H-pyrazolo[1,2-a]pyrazol-1-one and/or the addition salts thereof as the at least one first oxidation base and 4,5-diamino-1-(β-hydroxyethyl)pyrazole and/or the addition salts thereof as the at least one second oxidation base.

It is known practice to dye keratin fibers, for example human keratin fibers such as the hair, with dye compositions containing oxidation dye precursors, such as ortho- or para-phenylenediamines, ortho- or para-aminophenols, and heterocyclic compounds such as diaminopyrazole derivatives, pyrazolo[1,5-a]pyrimidine derivatives, pyrimidine derivatives, pyridine derivatives, indole derivatives and indoline derivatives, which are generally known as oxidation bases. Oxidation dye precursors, or oxidation bases, are colorless or weakly colored compounds which, when combined with oxidizing products, can give rise to colored or coloring compounds via a process of oxidative condensation. Permanent colorations may thus be obtained.

It is also known that the shades obtained with these oxidation bases may be varied by combining them with couplers or coloration modifiers, the latter being chosen for example from meta-phenylenediamines, meta-aminophenols, meta-hydroxyphenols and certain heterocyclic compounds.

The variety of molecules used as regards the oxidation bases and couplers allows a wide range of colors to be obtained.

The use of oxidation bases such as para-phenylenediamine and para-aminophenol derivatives can allow quite a broad range of colors to be obtained at basic pH, but may not always, however, simultaneously achieve shades with good chromaticity, while at the same time giving the hair excellent properties in terms of strength of color, uniformity of the color, and fastness with respect to external agents.

The use of these bases at neutral pH does not always allow a varied range of shades to be produced, for example warm shades such as reds and oranges.

Thus there is a need in the art to provide novel compositions for dyeing keratin fibers that make it possible to obtain a coloration with at least one of the following attributes: strong, powerful, chromatic, aesthetic, and sparingly selective red and/or coppery shades, and for example intermediate reddish-copper and coppery-red shades, showing good resistance to the various attacking factors to which the hair may be subjected, such as shampoos, light, sweat, and permanent-wave reshaping operations.

The present disclosure therefore relates to a composition for dyeing keratin fibers, comprising, in a suitable medium:
at least one first oxidation base chosen from 2,3-diamino-6,7-dihydro-1H,5H-pyrazolo[1,2-a]pyrazol-1-one of formula (I) and the addition salts thereof:

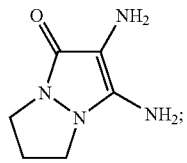

and
at least one second oxidation base chosen from 4,5-diamino-1-(β-hydroxyethyl)pyrazole and the addition salts thereof.

The present disclosure can make it possible to obtain coloring of the keratin fibers in strong and/or chromatic red and/or coppery shades. The intermediate coppery-red and reddish-copper shades obtained can be aesthetic with great strength and/or chromaticity.

The present disclosure can also make it possible to obtain sparingly selective colorations that show good resistance to the various attacks to which the hair may be subjected, such as shampoos, light, sweat, and permanent-wave reshaping operations. It furthermore can also make it possible to obtain strong colorations at neutral pH.

The present disclosure also relates to a process for dyeing keratin fibers using the composition of the present disclosure, the use of this composition for dyeing keratin fibers, and also a method for making the composition of the present disclosure.

The present disclosure also relates to a dyeing kit comprising, in a first compartment, a dye composition containing 2,3-diamino-6,7-dihydro-1H,5H-pyrazolo[1,2-a]pyrazol-1-one and/or a salt thereof as the at least one first oxidation base, and 4,5-diamino-1-(β-hydroxyethyl)pyrazole and/or a salt thereof as the at least one second oxidation base, and, in a second compartment, a composition containing at least one oxidizing agent.

Unless otherwise indicated, the limits of the ranges of values which are given in the context of the present disclosure are included in these ranges.

According to at least one embodiment, in the composition in accordance with the disclosure, the molar ratio of the at least one first oxidation base to the at least one second oxidation base has a value that ranges from 0.025 to 20, such as from 0.03 to 15, such as from 0.05 to 10.

The compositions of the disclosure may contain the at least one first oxidation base and/or the at least one second oxidation base, respectively, in the form of a mixture of several salts or of a mixture of a nonsalified compound with at least one salt.

The dye composition of the disclosure may contain at least one additional oxidation base that is different from the at least one first and the at least one second oxidation bases chosen from those conventionally used for dyeing keratin fibers.

The composition of the present disclosure may, for example, comprise at least one additional oxidation base chosen from para-phenylenediamines, bis(phenyl)alkylenediamines, para-aminophenols, bis-para-aminophenols, ortho-aminophenols, ortho-phenylenediamines and heterocyclic bases other than 2,3-diamino-6,7-dihydro-1H,5H-pyrazolo[1,2-a]pyrazol-1-one, 4,5-diamino-1-(β-hydroxyethyl)pyrazole, and the addition salts thereof.

Among the para-phenylenediamines, non-limiting mention may be made, by way of example, of para-phenylenediamine, para-toluenediamine, 2-chloro-para-phenylenediamine, 2,3-dimethyl-para-phenylenediamine, 2,6-dimethylpara-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(3-hydroxyethyl)-para-phenylenediamine, 4-N,N-bis(β-hydroxyethyl)amino-2-methylaniline, 4-N,N-bis(p-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-(β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and the addition salts thereof.

Among the para-phenylenediamines mentioned above, non-limiting mention may also be made of para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the addition salts thereof.

Among the bis(phenyl)alkylenediamines, non-limiting mention may be made, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and the addition salts thereof.

Among the para-aminophenols, non-limiting mention may be made, by way of example, of para-aminophenol, 3-methyl-4-aminophenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-β-hydroxyethylaminomethyl)phenol, 4-amino-2-fluorophenol, and the addition salts thereof.

Among the ortho-aminophenols, non-limiting mention may be made, by way of example, of 2-aminophenol, 2-amino-5-methylphenol, 2-amino-6-methylphenol, 5-acetamido-2-aminophenol, and the addition salts thereof.

Among the heterocyclic bases, non-limiting mention may be made, by way of example, of pyridine derivatives, pyrimidine derivatives, and pyrazole derivatives.

Among the pyridine derivatives, non-limiting mention may be made of the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, diaminopyridine, and the addition salts thereof.

Other pyridine oxidation bases that may be used in the present disclosure for example are the 3-aminopyrazolo[1,5-a]pyridine oxidation bases, or the addition salts thereof, described for example in patent application FR 2 801 308. By way of example, non-limiting mention may be made of pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridine-2-carboxylic acid; 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2-(3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxyethyl)amino]ethanol; 2-[(3-aminopyrazolo[1,5-a]pyrid-7-yl)(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyrid-6-ol; 3-aminopyrazolo[1,5-a]pyrid-7-ol; and also the addition salts thereof.

Among the pyrimidine derivatives, non-limiting mention may be made of the compounds described, for example, in patents DE 23 59 399; JP 88-169571; JP 05-63124; EP 0 770 375 or patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which non-limiting mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, and the addition salts thereof and tautomeric forms thereof, when a tautomeric equilibrium exists.

Among the pyrazole derivatives, non-limiting mention may be made of the compounds described in patents DE 38 43 892 and DE 41 33 957 and patent applications WO 94/08969, WO 94/08970, FR-A-2 733 749 and DE 195 43 988 such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof.

In at least one embodiment of the present disclosure, the composition disclosed herein comprises at least one additional oxidation base chosen from para-aminophenols and para-phenylenediamines. For example, among the para-aminophenols, para-aminophenol, 3-methyl-4-aminophenol, and the addition salts thereof can be used. For instance, among the para-phenylenediamines, para-phenylenediamine, para-toluenediamine, N,N-bis(β-hydroxyethyl)-para-phenylenediamine, and the addition salts thereof can be used.

The dye composition of the disclosure may also contain at least one coupler and/or the addition salts thereof conventionally used for dyeing keratin fibers.

The composition of the present disclosure may, for example, thus comprise at least one coupler chosen from meta-phenylenediamines, meta-aminophenols, meta-diphenols, naphthalene couplers, heterocyclic couplers, and/or the addition salts thereof.

By way of example of the at least one coupler, non-limiting mention may be made of 3-aminophenol, 2-methyl-5-aminophenol, 2-methyl-5-(β-hydroxyethylamino)phenol, 2-chloro-6-methyl-3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and the addition salts thereof.

In at least one embodiment, the composition in accordance with the disclosure comprises at least one additional coupler chosen from meta-aminophenols. For example, the composition in accordance with the disclosure may comprise at least one additional coupler chosen from 2-chloro-6-methyl-3-aminophenol, 2-methyl-5-aminophenol, 2-methyl-5-(β-hydroxyethylamino)phenol, and the addition salts thereof.

The at least one first oxidation base, the at least one second oxidation base, and the at least one additional oxidation base may each be present in the composition of the disclosure in an amount ranging from 0.001% to 10% by weight, relative to the total weight of the dye composition, such as from 0.005% to 6%.

The at least one coupler may be present in the composition of the disclosure in an amount, for each coupler, ranging from 0.001% to 10% by weight, relative to the total weight of the dye composition, such as from 0.005% to 6%.

In general, the addition salts of the oxidation bases and of the couplers that can be used in the context of the disclosure are for example chosen from the addition salts with an acid, such as the hydrochlorides, hydrobromides, sulfates, citrates, succinates, tartrates, lactates, ($C_1$-$C_4$)alkylsulfonates, and for example methylsulfonates, tosylates, benzenesulfonates, phosphates and acetates, and the addition salts with a base, such as sodium hydroxide, potassium hydroxide, aqueous ammonia, amines or alkanolamines.

The medium that is suitable for dyeing, also known as a dye support, is a cosmetic medium generally constituted of water or of a mixture of water and at least one organic solvent. By way of organic solvent, non-limiting mention may, for example, be made of $C_1$-$C_4$ lower alkanols, such as ethanol and isopropanol; polyols and polyol ethers such as 2-butoxyethanol, propylene glycol, propylene glycol monomethyl ether, diethylene glycol monoethyl ether and diethylene glycol monomethyl ether, and also aromatic alcohols such as benzyl alcohol or phenoxyethanol, and mixtures thereof.

The solvents may for example be present in an amount ranging from 1% to 40% by weight, relative to the total weight of the dye composition, for example from 5% to 30% by weight.

The dye composition in accordance with the disclosure may also contain at least one adjuvant chosen from the various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, and for instance anionic, cationic, nonionic and amphoteric associative polymeric thickeners, antioxidants, penetrating agents, sequestering agents, fragrances, buffers, dispersing agents, conditioning agents, such as for example silicones, which may be volatile or non-volatile, and modified or unmodified, film-forming agents, ceramides, preservatives, and opacifiers.

The at least one adjuvant may be present in an amount, for each adjuvant, ranging from 0.01% to 20% by weight, relative to the weight of the dye composition.

Of course, those skilled in the art will take care to select this or these optional additional compound(s) in such a way that the beneficial properties intrinsically associated with the oxidation dye composition in accordance with the disclosure are not, or are not substantially, impaired by the addition(s) envisaged.

The pH of the dye composition in accordance with the disclosure generally ranges from 3 to 12, for example from 5 to 11. It may be adjusted to the desired value using acidifying or basifying agents normally used in the dyeing of keratin fibers, or alternatively using standard buffer systems.

Among the acidifying agents, non-limiting mention may be made, by way of example, of inorganic or organic acids such as hydrochloric acid, orthophosphoric acid, sulfuric acid, carboxylic acids such as acetic acid, tartaric acid, citric acid or lactic acid, and sulfonic acids.

Among the basifying agents, non-limiting mention may be made, by way of example, of aqueous ammonia, alkali metal carbonates, alkanolamines such as mono-, di- and triethanolamines and also derivatives thereof, sodium hydroxide, potassium hydroxide and the compounds of formula (II):

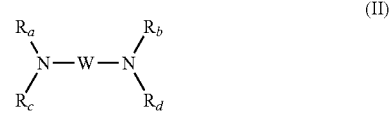

(II)

in which W is a propylene residue optionally substituted with a hydroxyl group or a $C_1$-$C_4$ alkyl radical; and $R_a$, $R_b$, $R_c$ and $R_d$, which may be identical or different, represent a hydrogen atom, a $C_1$-$C_4$ alkyl radical, or a $C_1$-$C_4$ hydroxyalkyl radical.

The dye composition according to the disclosure may be in various forms, such as in the form of liquids, creams, or gels, or in any other form that is suitable for dyeing keratin fibers such as human hair.

The present disclosure also relates to a process for dyeing keratin fibers, comprising:
applying to the keratin fibers a composition comprising, in a suitable medium, at least one first oxidation base chosen from 2,3-diamino-6,7-dihydro-1H,5H-pyrazolo[1,2-a]pyrazol-1-one and the addition salts thereof; and at least one second oxidation base chosen from 4,5-diamino-1-(β-hydroxyethyl)pyrazole and the addition salts thereof in the presence of at least one oxidizing agent; and leaving the resultant composition on the keratin fibers for a period of time that is sufficient to develop the desired coloration. The color is developed using at least one oxidizing agent. The color may be developed at acidic, neutral, or alkaline pH, and the at least one oxidizing agent may be added to the composition of the disclosure just at the time of use, or it may be used starting from an oxidizing composition containing it, which is applied simultaneously with or sequentially to the composition disclosed herein.

According to at least one embodiment, the composition according to the present disclosure is mixed, for example at the time of use, with a composition containing, in a medium that is suitable for dyeing, at least one oxidizing agent, the at least one oxidizing agent being present in an amount that is sufficient to develop a coloration. The "ready-to-use" mixture obtained is then applied to the keratin fibers. After a leave-in time ranging from 3 to 50 minutes, for example 5 to 30 minutes, the keratin fibers are rinsed, washed with shampoo, rinsed again, and then dried.

The oxidizing agents conventionally used for the oxidation dyeing of keratin fibers are, for example, hydrogen peroxide, urea peroxide, alkali metal bromates, persalts such as perborates and persulfates, peracids and oxidase enzymes, among which non-limiting mention may be made of peroxidases, 2-electron oxidoreductases such as uricases, and 4-electron oxygenases such as laccases. For example, hydrogen peroxide can be used in at least one embodiment.

The oxidizing composition may also contain at least one adjuvant chosen from the various adjuvants conventionally used in compositions for dyeing the hair and as defined herein.

The pH of the oxidizing composition containing the at least one oxidizing agent is such that, after mixing with the dye composition, the pH of the resulting composition applied to the keratin fibers for example can range from 3 to 12, such as from 5 to 11. It may be adjusted to the desired value via acidifying or basifying agents normally used in the dyeing of keratin fibers and as defined herein.

The ready-to-use composition that is applied to the keratin fibers may be in various forms, such as in the form of liquids, creams, or gels or any other form suitable for dyeing keratin fibers such as human hair.

The present disclosure also relates to a multi-compartment dyeing device or "kit", in which a first compartment contains the dye composition of the present disclosure as defined herein with the exception of the at least one oxidizing agent, and a second compartment contains an oxidizing composition. This device may be equipped with an applicator for applying the desired mixture to the hair, such as the devices described in patent FR-2 586 913. The multi-compartment device for dyeing keratin fibers thus comprises:

a first compartment containing a dye composition comprising, in a suitable medium:

at least one first oxidation base chosen from 2,3-diamino-6,7-dihydro-1H,5H-pyrazolo[1,2-a]pyrazol-1-one and the addition salts thereof; and at least one second oxidation base chosen from 4,5-diamino-1-(β-hydroxyethyl)pyrazole and the addition salts thereof, and a second compartment containing at least one oxidizing agent.

The present disclosure also relates to a method for making a composition for dyeing keratin fibers comprising combining, in a suitable medium:

at least one first oxidation base chosen from 2,3-diamino-6,7-dihydro-1H,5H-pyrazolo[1,2-a]pyrazol-1-one and the addition salts thereof; and at least one second oxidation base chosen from 4,5-diamino-1-(β-hydroxyethyl)pyrazole and the addition salts thereof wherein the ingredients can be added in any order.

The examples which follow serve to illustrate the disclosure without, however, being limiting in nature.

EXAMPLE 1

The following dye composition was prepared (amounts expressed with respect to the total weight of the composition, unless otherwise indicated):

| | |
|---|---|
| Lauryl alcohol comprising 12 EO | 7 g |
| Decyl alcohol comprising 3 EO | 10 g |
| Oleocetyl alcohol comprising 30 EO | 4 g |
| Cetylstearyl alcohol | 11.5 g |
| Lauric acid | 3 g |
| Glycol distearate | 2 g |
| AEROSIL R 972 (Degussa) | 1.2 g |
| CARBOPOL 980 (Lubrizol) | 0.4 g |
| Propylene glycol | 10 g |
| Monoethanolamine | 1.6 g |
| MEXOMERE PO (Chimex) | 3 g AM |
| MERQUAT 280 (Nalco) | 2.2 g AM |
| Sequestering agent, antioxidant, reducing agent, fragrance | q.s. |
| Aqueous ammonia (20% of $NH_3$) | 10 g |
| 2,3-diamino-6,7-dihydro-1H,5H-pyrazolo[1,2-a]pyrazol-1-one, 2 $CH_3$—$SO_3H$ | 0.3 g |
| 4,5-diamino-1-(β-hydroxyethyl)pyrazole, sulfate | 1.7 g |
| 2-chloro-6-methyl-3-aminophenol | 0.3 g |
| Para-phenylenediamine | 0.42 g |
| Para-aminophenol | 0.2 g |
| 2-methyl-5-aminophenol | 1.4 g |
| Water | q.s. 100 g |

AM = Active material

At the time of use, 1 part by weight of the Example 1 dye composition was mixed with 1.5 parts by weight of a 20-volumes hydrogen peroxide solution at pH 2.2. A final pH close to 9.6 was obtained.

The mixture obtained was applied to locks of grey hair containing 90% white hairs. After a leave-on time of 30 minutes at ambient temperature, the locks were rinsed, washed with a standard shampoo, rinsed again and then dried.

The hair coloration was evaluated visually. A sparingly selective, chromatic, coppery-red blonde shade was obtained.

EXAMPLE 2

The following dye composition was prepared (amounts expressed with respect to the total weight of the composition, unless otherwise indicated):

| | |
|---|---|
| Lauryl alcohol comprising 12 EO | 7 g |
| Decyl alcohol comprising 3 EO | 10 g |
| Oleocetyl alcohol comprising 30 EO | 4 g |
| Cetylstearyl alcohol | 11.5 g |
| Lauric acid | 3 g |
| Glycol distearate | 2 g |
| AEROSIL R 972 (Degussa) | 1.2 g |
| CARBOPOL 980 (Lubrizol) | 0.4 g |
| Propylene glycol | 10 g |
| Monoethanolamine | 1.6 g |
| MEXOMERE PO (Chimex) | 3 g AM |
| MERQUAT 280 (Nalco) | 2.2 g AM |
| Sequestering agent, antioxidant, reducing agent, fragrance | q.s. |
| Aqueous ammonia (20% of NH$_3$) | 10 g |
| 2,3-diamino-6,7-dihydro-1H,5H-pyrazolo[1,2-a]pyrazol-1-one, 2 CH$_3$—SO$_3$H | 0.3 g |
| 4,5-diamino-1-(β-hydroxyethyl)pyrazole, sulfate | 1.7 g |
| 2-chloro-6-methyl-3-aminophenol | 0.3 g |
| 2-methyl-5-aminophenol | 1.0 g |
| Water | q.s. 100 g |

AM = Active material

At the time of use, 1 part by weight of the Example 2 dye composition was mixed with 1.5 parts by weight of a 20-volumes hydrogen peroxide solution at pH 22. A final pH close to 9.6 was obtained.

The mixture obtained was applied to locks of grey hair containing 90% white hairs. After a leave-on time of 30 minutes at ambient temperature, the locks were rinsed, washed with a standard shampoo, rinsed again and then dried.

The hair coloration was evaluated visually. A sparingly selective, chromatic, coppery-red shade was obtained.

What is claimed is:

1. A composition for dyeing keratin fibers, comprising, in a suitable medium:
    at least one first oxidation base chosen from 2,3-diamino-6,7-dihydro-1H,5H-pyrazolo[1,2-a]pyrazol-1-one and the addition salts thereof; and
    at least one second oxidation base chosen from 4,5-diamino-1-(β-hydroxyethyl)pyrazole and the addition salts thereof wherein the molar ratio of the at least one first oxidation base to the at least one second oxidation base has a value that ranges from 0.025 to 20.

2. A composition according to claim 1, wherein the molar ratio of the at least one first oxidation base to the at least one second oxidation base has a value that ranges from 0.03 to 15.

3. A composition according to claim 2, wherein the molar ratio of the at least one first oxidation base to the at least one second oxidation base has a value that ranges from 0.05 to 10.

4. A composition according to claim 1, further comprising at least one additional oxidation base chosen from para-aminophenols and para-phenylenediamines.

5. A composition according to claim 4, wherein the at least one additional oxidation base is chosen from para-aminophenol, 3-methyl-4-aminophenol, and the addition salts thereof.

6. A composition according to claim 4, wherein the at least one additional oxidation base is chosen from para-phenylenediamine, para-toluenediamine, N,N-bis(β-hydroxyethyl)-para-phenylenediamine, and the addition salts thereof.

7. A composition according to claim 1, wherein the at least one first oxidation base and the at least one second oxidation base are each present in an amount ranging from 0.001% to 10% by weight, relative to the total weight of the composition.

8. A composition according to claim 1, further comprising at least one coupler.

9. A composition according to claim 8, wherein the at least one coupler is chosen from meta-aminophenols.

10. A composition according to claim 9, wherein the at least one coupler is chosen from 2-chloro-6-methyl-3-aminophenol, 2-methyl-5-aminophenol, 2-methyl-5-(β-hydroxyethylamino)phenol, and the addition salts thereof.

11. A composition according to claim 1, further comprising at least one oxidizing agent.

12. A process for dyeing keratin fibers, comprising:
    applying to the keratin fibers a composition comprising, in a suitable medium,
        at least one first oxidation base chosen from 2,3-diamino-6,7-dihydro-1H,5H-pyrazolo[1,2-a]pyrazol-1-one and the addition salts thereof; and
        at least one second oxidation base chosen from 4,5-diamino-1-(β-hydroxyethyl)pyrazole and the addition salts thereof
    in the presence of at least one oxidizing agent; and
    leaving the resultant composition on the keratin fibers for a period of time that is sufficient to develop the desired coloration wherein the molar ratio of the at least one first oxidation base to the at least one second oxidation base has a value that ranges from 0.025 to 20.

13. A multi-compartment device for dyeing keratin fibers, comprising
    a first compartment containing a dye composition comprising, in a suitable medium:
        at least one first oxidation base chosen from 2,3-diamino-6,7-dihydro-1H,5H-pyrazolo[1,2-a]pyrazol-1-one and the addition salts thereof; and
        at least one second oxidation base chosen from 4,5-diamino-1-(β-hydroxyethyl)pyrazole and the addition salts thereof,
    and
    a second compartment containing at least one oxidizing agent wherein the molar ratio of the at least one first oxidation base to the at least one second oxidation base has a value that ranges from 0.025 to 20.

14. A method for making a composition for dyeing keratin fibers comprising combining, in a suitable medium:
    at least one first oxidation base chosen from 2,3-diamino-6,7-dihydro-1H,5H-pyrazolo[1,2-a]pyrazol-1-one and the addition salts thereof; and
    at least one second oxidation base chosen from 4,5-diamino-1-(β-hydroxyethyl)pyrazole and the addition salts thereof
    wherein the ingredients can be added in any order wherein the molar ratio of the at least one first oxidation base to the at least one second oxidation base has a value that ranges from 0.025 to 20.

* * * * *